(12) United States Patent
Ruton

(10) Patent No.: US 6,173,711 B1
(45) Date of Patent: Jan. 16, 2001

(54) RESPIRATORY ASSISTANCE DEVICE

(75) Inventor: Stéphane Ruton, Viroflay (FR)

(73) Assignee: Taema, Antony Cedex (FR)

( * ) Notice: Under 35 U.S.C. 154(b), the term of this patent shall be extended for 0 days.

(21) Appl. No.: 08/956,784

(22) Filed: Oct. 23, 1997

(30) Foreign Application Priority Data

Oct. 30, 1996 (FR) .................................................. 9613265

(51) Int. Cl.$^7$ .................................................. A61M 16/00
(52) U.S. Cl. .............................. 128/204.26; 128/205.24; 128/204.25
(58) Field of Search .................... 128/204.25, 204.26, 128/205.24

(56) References Cited

U.S. PATENT DOCUMENTS

| | | | |
|---|---|---|---|
| 3,486,502 | * 12/1969 | Wilson | 128/205.24 |
| 3,598,116 | * 8/1971 | Peters et al. | 128/204.25 |
| 3,964,476 | * 6/1976 | Palleni | 128/205.24 |
| 4,082,093 | * 4/1978 | Fry et al. | 128/204.25 |
| 4,177,830 | * 12/1979 | Munson | 128/205.24 |
| 4,224,940 | * 9/1980 | Monnier | 128/205.24 |
| 4,227,519 | * 10/1980 | Warnow et al. | 128/205.24 |
| 4,245,633 | * 1/1981 | Erceg | 128/205.24 |
| 4,401,115 | * 8/1983 | Monnier | 128/205.24 |
| 4,417,573 | * 11/1983 | Devries | 128/204.25 |
| 4,452,242 | * 6/1984 | Banziger | 128/205.24 |
| 4,611,591 | * 9/1986 | Inui et al. | 128/205.24 |
| 5,303,699 | * 4/1994 | Bonassa et al. | 128/205.21 |
| 5,503,146 | 4/1996 | Froehlich et al. | 128/204.23 |
| 5,542,416 | * 8/1996 | Chalvignac | 128/205.24 |
| 5,664,562 | * 9/1997 | Bourdon | 128/204.24 |

FOREIGN PATENT DOCUMENTS

| | | |
|---|---|---|
| 0 691 134 | 1/1996 | (EP) . |
| 2 714 837 | 7/1995 | (FR) . |
| WO 94/06499 | 3/1994 | (WO) . |

* cited by examiner

*Primary Examiner*—Aaron J. Lewis
(74) *Attorney, Agent, or Firm*—Young & Thompson

(57) ABSTRACT

A respiratory assistance device, includes an inhalation branch (2) which is permanently connected, at its upstream end, to a first source (1) of a flow of pressurized gas and, at its downstream end, to a user's airway; at least a first (9) and a second (3) exhalation valve, these being arranged on the respiratory branch (2) and controlled so that they are closed during the inhalation phase; a detection unit (10) which, in proximity to the downstream end of the inhalation branch, detects the user's respiratory activity and sends a respiratory-activity data item to drive element (12), the drive element (12) controlling the first gas flow source (1) in such a way as to deliver a gas stream with substantially constant non-zero flow rate to the inhalation branch (2) throughout the exhalation phase.

16 Claims, 2 Drawing Sheets

RESPIRATORY ASSISTANCE DEVICE

FIELD OF THE INVENTION

The present invention relates to a respiratory assistance device which has two pressure levels and can be used in the context of respiratory assistance at home or in a hospital environment.

BACKGROUND OF THE INVENTION

Conventionally, respiratory assistance consists in ventilating a patient using a pressurized gas, for example air or oxygen-enriched air, that is to say, during the inhalation phase which is usually initiated by the patient, in applying a constant positive pressure in the "patient" circuit of a breathing appliance.

The "patient" circuit usually consists of ducting elements which make it possible to connect the patient's airways to the pressurized gas source; the patient circuit therefore comprises elements such as the breathing duct or ducts, a breathing mask or goggles, and a tracheotomy tube.

The pressure in the patient circuit varies depending on the respiratory phase: inhalation phase or exhalation phase. Specifically, during the inhalation phase, the pressurized gas output by a gas flow source, or turbine, is distributed to the patient's airways at a given inhalation pressure, whereas during the exhalation phase, the exhalation initiated by the patient is passive and takes place at atmospheric pressure or at a given positive exhalation pressure, or PEP; the exhaled gases are discharged either through one (or more) exhalation valves arranged on the patient circuit, or through holes or ports arranged in the breathing mask.

Respiratory assistance devices operating on this principle are commonly referred to as respiratory assistance devices having two pressure levels.

It has been observed that discharging the exhalation gases, which are rich in $CO_2$, via holes or ports made in the breathing mask had the major drawback of not allowing full discharge of the exhaled gases, which tend to build up in certain parts of the patient circuit, in particular in the breathing mask. During the following inhalation phase, a build-up of this type leads to re-inhalation of the gases which are rich in $CO_2$, which is a problem for the patient.

Respiratory assistance devices having two pressure levels which are equipped with one or more exhalation valves are therefore preferred.

Mention may be made of EP-B-0,317,417, which describes a respiration assistance device in which the patient circuit comprises a pneumatically controlled exhalation valve. During the inhalation phase, the control inlet of this valve is subjected to the pressure of a pressurized flow source which closes the exhalation valve and allows the patient circuit to be connected in a leak-tight fashion to the pressurized gas flow source. When a significant reduction in the inhaled flowrate is detected, control electronics fully suspends the operation of the pressurized flow source, the structure of which is such that its outlet orifice is then returned to atmospheric pressure, which pressure is applied to the exhalation valve and thus allows it to open.

EP-A-0,425,092 relates to a respiration aid device which, in place of the exhalation valve, includes a calibrated permanent-leakage orifice, while the pressure of a flow source is set to two different levels depending on whether the phase is an inhalation phase or an exhalation phase.

In other words, this type of known device of the prior art has a mode of operation which is based on at least partially, and generally fully, interrupting the gas flow source during the exhalation phase. However, any stopping of the gas flow source has a major drawback, namely that when changing from an exhalation phase to the next inhalation phase, the pressure rise time of the patient circuit depends closely, on the one hand, on the power of the gas flow source and, on the other hand, on its mechanical inertia.

The result of this is that, in order to perform well and be efficient, and to overcome these problems, these devices necessarily need to be provided with a powerful gas flow source having little mechanical inertia. However, the gas flow sources currently available on the market which make it possible to meet such specifications of power and inertia, usually have drawbacks which are incompatible with use at home, and more generally in the medical field: excessive bulk, noise pollution, etc.

Furthermore, known respiratory assistance devices also sometimes have another drawback, namely that they do not allow the exhaled gas to be discharged properly.

Indeed, in order to prevent the exhalation gas, which is rich in $CO_2$, from passing along the patient circuit during the exhalation phase, and then being re-inhaled during the following inhalation phase, it is recommended for a flow of gas to be maintained in the patient circuit, between the flow source and the patient; this flow makes it possible to remove the exhaled gases.

It is easy to see that, if the communication between the gas flow source and the patient is fully interrupted during the exhalation phase, there can be no circulation gas in the patient circuit, and there is a risk of the exhalation gases building up.

A partial solution to these problems is provided by WO-A-94/06499, which describes a respiration aid device comprising a patient circuit having an inhalation branch connected to a pressurized inhalation flow source, and an exhalation branch equipped with an exhalation valve which is controlled in such a way that it is closed during inhalation.

According to a first embodiment of this device, drive means control, on the one hand, distribution means and, on the other hand, the interruption of the communication between the inhalation flow source and the inhalation branch of the patient circuit, when a sensor detects that the patient is preparing for an exhalation phase; the communication between the inhalation flow source and the inhalation branch is reestablished when changing to an inhalation phase, by controlling the distribution means. In other words, throughout the exhalation phase, the inhalation flow source is kept in operation such as to provide the inhalation flow.

It is easy to see that this embodiment is not satisfactory because, during the exhalation phase, the flow source continues to distribute pressurized gas, and this will build up in the patient circuit between the flow source and the site where the communication is interrupted. This build-up of gas will result in an upstream overpressure of the patient circuit, and on entering the following inhalation phase and after re-establishing the said communication, this overpressure will propagate to the patient's lungs, which will then suffer a harmful "pulmonary respiratory shock" due to this overpressure. Furthermore, since the gas distributed by the flow source during the exhalation phase is not removed, the said flow source is subject to damage, in particular through heating. Finally, this embodiment does not solve the problem of the exhaled gases building up, since the communication between the flow source and the breathing mask is interrupted during the exhalation phase.

In order to try to overcome these problems, WO-A-94/06499 proposes a second embodiment, implementing a leakage-compensation duct which, during the exhalation phase, makes it possible to channel a fraction of the gas delivered by the respiratory source to a site in the patient circuit lying downstream of the site where the communication is interrupted. However, although this solution allows a partial solution to the problems of damage to the flow source and removing the exhaled gases, it nevertheless has several other drawbacks.

Specifically, the bypass duct has an unalterable constant diameter and is not therefore suited to all values of flow rate, for example according to whether the patient to be ventilated is an adult or child.

Thus, when the gas flow delivered by the flow source becomes too great for the bypass duct to fulfil its role properly, because its diameter is too small in comparison with the flow rate, the above problems of overpressure, risks of "pulmonary respiratory shock" and damage to the flow source again arise. Conversely, when the delivered gas flow rate becomes less than a certain threshold value, the bypass duct will allow an excessive quantity of gas to pass to the patient during the exhalation phase, and this will counteract proper exhalation and satisfactory removal of the gas, which is enriched in $CO_2$, exhaled by the patient.

SUMMARY OF THE INVENTION

To sum up, the solutions advocated by this document are not satisfactory. It is therefore necessary to develop new equipment to make it possible to overcome the problems mentioned above, without having the drawbacks of the prior art devices. The object of the present invention, within this context, is therefore to propose a respiration assistance device which has two compression levels and makes it possible to overcome the drawbacks of the prior art devices, and in particular:

- to minimize the pressure rise time of the patient circuit as far as possible when changing from an exhalation phase to the following inhalation phase;
- to eliminate any interruption of the communication in the patient circuit during the exhalation phases;
- its use for respiratory assistance both at home and in a hospital environment;
- efficient removal of the exhaled gases during the exhalation phase;
- to avoid any "pulmonary respiratory shock" when changing from an exhalation phase to a following inhalation phase;
- to eliminate any fitting of additional leak-compensation ducts in the patient circuit, while having a simple design and a moderate cost.

The invention therefore relates to a respiratory assistance device, comprising:

- an inhalation branch which is permanently connected, at its upstream end, to a first source of a flow of pressurized gas and, at its downstream end, to a user's airways,
- at least a first and a second exhalation valve, these being arranged on the respiratory branch and controlled so that they are closed during the inhalation phase,
- a detection means which, in proximity to the downstream end of the inhalation branch, detects the user's respiratory activity and sends a respiratory-activity data item to drive means, the drive means controlling the first gas flow source in such a way as to deliver a gas stream with substantially constant non-zero flowrate to the inhalation branch throughout the exhalation phase.

Preferably, the drive means control the first gas flow source in such a way as to deliver a gas stream to the inhalation branch with a flowrate, during the exhalation phase, which is substantially equal to the flowrate delivered at the end of the preceding inhalation phase.

Advantageously, at least a first exhalation valve is arranged in proximity to the upstream end of the inhalation branch and/or at least a second exhalation valve is arranged in proximity to the downstream end of the inhalation branch.

According to a preferred embodiment, the device of the invention furthermore includes a second pressurized gas flow source and a distribution means, the said second flow source and the said distribution means being controlled by the drive means.

It is preferable if the detection means is a pressure sensor which can be installed in the mask or simply connected to it by means of pressure take-off means, the exhalation valves are pneumatic valves having balloons and/or the distribution means is a solenoid valve.

Advantageously, during the inhalation phase, the solenoid valve establishes communication between the first pressurized gas flow source and the balloons of the pneumatic valves, so as to close the valves throughout the inhalation phase and/or during the exhalation phase, the solenoid valve establishes communication between the second pressurized gas flow source and the balloons of the pneumatic valves, so as to control the opening of the valves.

Preferably, the flowrate from the second gas source is less than the flowrate from the first pressurized gas source.

If needed, a fraction of the gas delivered by the second pressurized gas source is discharged to the atmosphere via a vent.

Advantageously, the pressurized gas is air or oxygen-enriched air.

Furthermore, the invention also relates to a method for using the device according to the present invention characterized in that the control voltage of the first flow source is kept at a substantially constant and non-zero value throughout the exhalation phase.

Preferably, throughout the exhalation phase, the control voltage of the first flow source is kept at a value substantially equal to the value which it had at the end of the preceding inhalation phase.

Advantageously, the exhalation is carried out under positive exhalation pressure.

BRIEF DESCRIPTION OF THE DRAWINGS

The invention will now be described in more detail with the aid of an embodiment of the invention, with reference to the appended figures which are given solely by way of illustration and without implying any limitation.

DETAILED DESCRIPTION OF THE DRAWINGS

Figure 1:
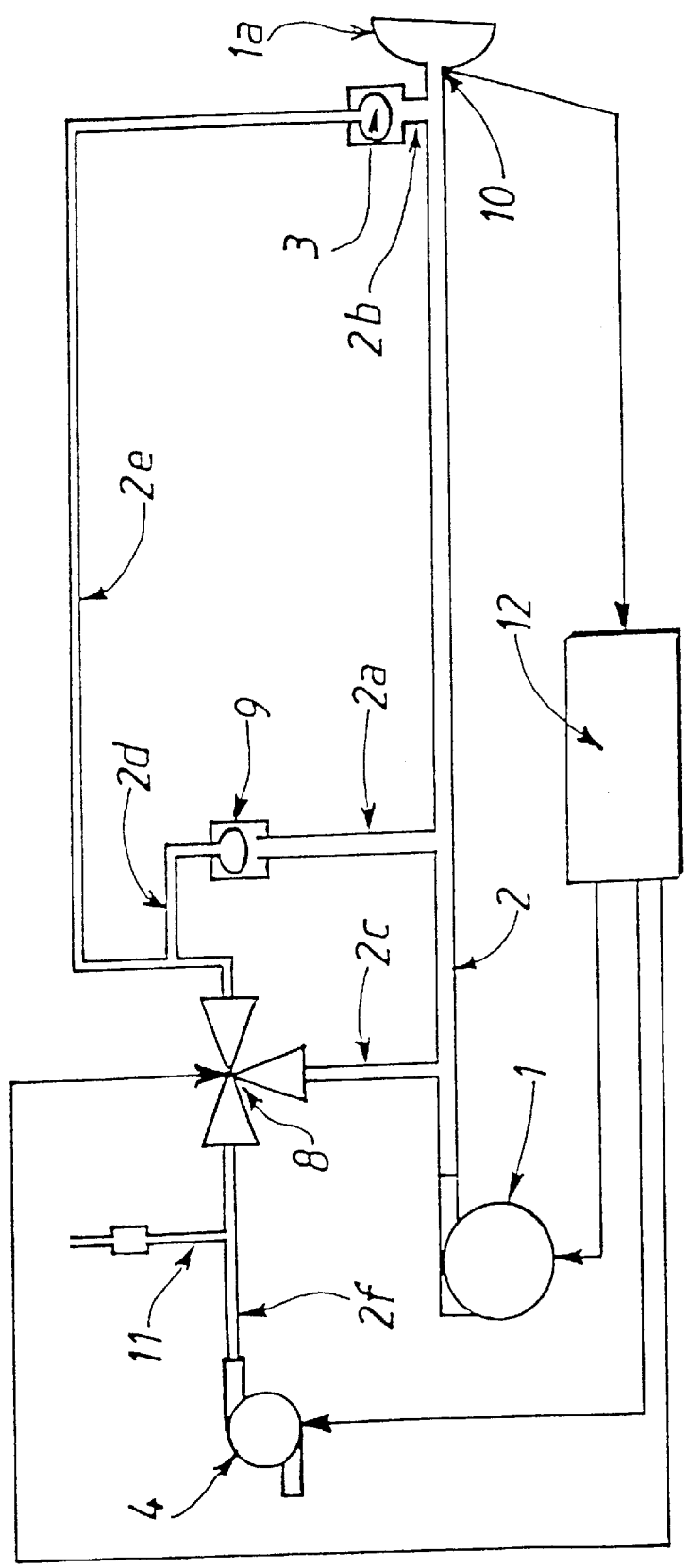
FIG. 1 represents a diagram of an embodiment of a respiratory assistance device according to the invention.

A respiratory assistance device according to the invention is represented in FIG. 1.

In this FIG. 1, the respiratory branch 2 is connected by one of its ends to a first pressurized gas flow source 1, for example a turbine delivering a gas at a pressure, for example, in the range 0 to 50 mbar, and by its other end to the patient's airways, via a breathing mask 1a. Two valves 3 and 9 having balloons are arranged on the inhalation branch 2, so that they are closed during the inhalation phases in order to prevent the pressurized gas output by the first gas flow source 1 from being sent to the atmosphere.

The balloon-type valve 9 is arranged upstream of the inhalation branch 2, that is to say close to the pressurized gas flow source 1, whereas the balloon-type valve 3, for its part, is arranged downstream of the inhalation branch 2, that is to say as close as possible to the patient's airways, for example level with the breathing mask 1*a*.

The device represented in FIG. 1 also has a solenoid valve 8 which is intended to establish communication between the inhalation branch 2, via a bypass 2*c*, and the ducts 2*d* and 2*e* which are connected to the balloons of the valves 9 and 3, respectively, so as to allow them to be closed during the inhalation phases.

During the exhalation phases, the solenoid valve 8 is driven by the drive means 12 in such a way as to establish communication between the balloons 9 and 3, via the ducts 2*d* and 2*e*, respectively, and a second gas flow source 4 which delivers gas at a pressure which, for example, is in the range 0 to 10 mbar, via the duct 2*f*. Thus, given that the second flow source 4 is also controlled by the drive means 12, it is easy to control the pressure in the balloons of the valves 9 and 3, and thereby the positive exhalation pressure (PEP), that is to say the minimum pressure which the patient needs to exert (when exhaling) in order to allow the inhalation branch 2 to be connected to the atmosphere, by opening the valves 9 and 3 during the exhalation phases. A duct 11 for venting to the atmosphere is arranged on the duct 2*f*, between the solenoid valve 8 and the second flow source 4, commonly referred to as a "pump", in order to discharge to the atmosphere:

during the inhalation phases, the gas distributed continuously by the second flow source 4;

during the exhalation phases, any excess of gas in the ducts 2*f*, 2*d* or 2*e*, in order to prevent a possible overpressure in the balloons 9 and 3 and therefore a PEP which is too high and harmful to the patient.

The first pressurized gas flow source 1, the second flow source 4 and the solenoid valve 8 are driven by drive means 12 which are connected to a pressure sensor 10 arranged in or close to the breathing mask 1*a*.

The operation of drive means 12 during the various respiratory phases is described in detail below, with reference to FIGS. 2 and 3.

The type of respiratory phase, namely inhalation phase or exhalation phase, is determined using the sensor 10, which sends a respiratory phase signal (inhalation or exhalation) to the drive means 12. By way of example, use may be made of a sensor of the SENSYM® type (0 to 20 mbar) or any other respiratory-phase detection device, for example the one described in EP 0,505,232.

Throughout the inhalation phase, the sensor 10 measures the inhalation pressure, and this will be compared with a preset inhalation pressure value. So long as the difference between the preset inhalation pressure value and the measured inhalation pressure value remains proportional to a given value, corresponding to a pressure value for the inhalation phase, the drive means 12 control the first flow source 1, the second flow source 4 and the solenoid 8 in such a way as to:

maintain communication between the inhalation branch 2 and the balloons of the valves 9 and 3 via the ducts 2*c*, 2*d* and 2*e*, in order to keep the valves 9 and 3 closed;

keep the control voltage of the first flow source 1 constant in order to deliver pressurized gas to the patient's airways via the inhalation branch 2;

and keep the control voltage of the second flow source 4 at a constant value, at a zero value or at a preset non-zero value, as required. Within the scope of the present invention, a non-zero preset value is preferred.

Figure 2:
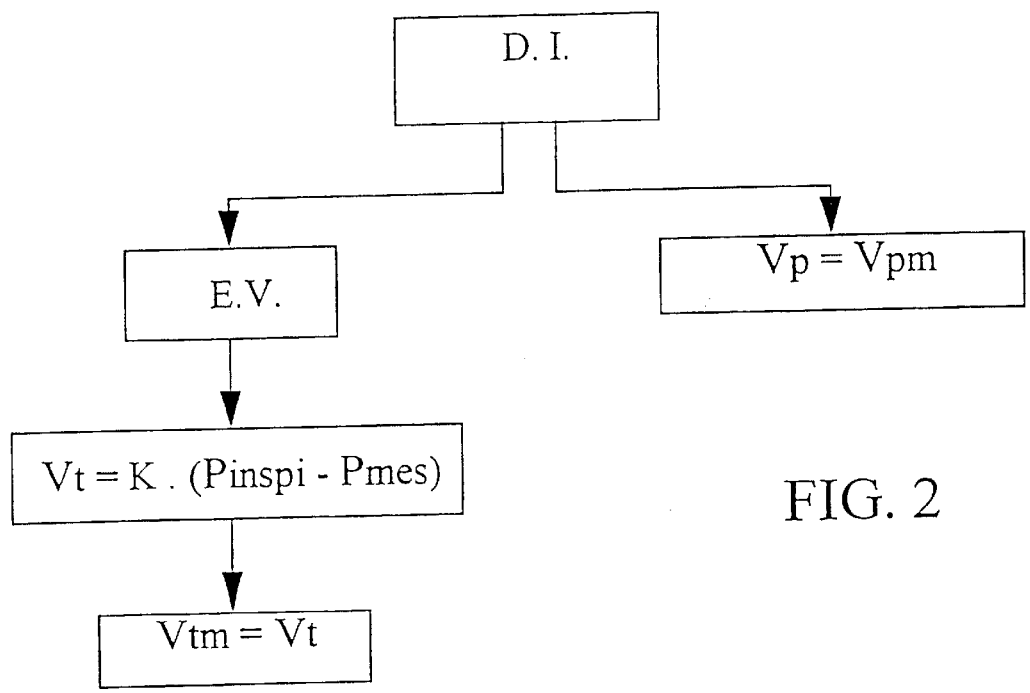
FIGS. 2 and 3 represent flow charts of the operation of a respiratory assistance device according to the invention, during an inhalation and during an exhalation phase, respectively.

This mode of operation is schematized on the flow chart in FIG. 2. More precisely there are two consequences to the detection of inspiration (D. I.), that is to say an inhalation signal. On the one hand, the control voltage (Vp) of the second flow source 4 is kept at its mean voltage value (Vpm), which was stored during the preceding exhalation phase, and, on the other hand, after the solenoid valve (S. V.) 8 has been switched, the control voltage (Vt) of the first flow source 1 is kept at a value proportional (coefficient K) to the difference between the setpoint pressure value (Pinh) during the inhalation phase and the measured pressure value (Pmes). The stored mean value of the control voltage (Vtm) of the first flow source is then equal to Vt.

When the difference between the set inhalation pressure and the measured inhalation pressure corresponds to a preset value for the end of an inhalation phase, the drive means 12 interrupt communication between the inhalation branch 2 and the balloons of the valves 9 and 3, and establish communication between the balloons and the second flow source 4 in order to make it possible to regulate the quantity of gas trapped in the balloons, and therefore the PEP. This pressure regulation is controlled by the drive means 12, which act on the second flow source 4. In order to eliminate the overpressure existing in the balloons 9 and 3 during the inhalation phase (valves closed), the drive means act on the second flow source 4 in such a way as to reduce its flow rate. It is then possible for the excess of gas (overpressure) in the balloons 9 and 3 to escape to the atmosphere via the vent 11, which makes it easier to open the balloon-type valves 9 and 3, owing to a lower PEP.

Furthermore, at the end of the inhalation phase, the drive means 12 store the value of the control voltage of the first flow source 1.

Next, during the exhalation phase, the control voltage of the first flow source 1 is kept constant, at the said value which it had at the end of the preceding inhalation phase.

The opening of the balloon-type valves 9 and 3 is regulated in such a way as to allow the pressurized gas to escape from the inhalation branch 2 through the valve 9, via the duct 2*a* and, to a lesser extent, through the balloon-type valve 3 via the duct 2*b*. The gases, rich in $CO_2$, which are exhaled by the patient are, for their part, discharged under controlled PEP through the balloon-type valve 3 and via the duct 2*b*. They cannot therefore stagnate or travel further along the inhalation branch.

The drive means 12 also control the voltage of the second flow source 4. In the same way as before, on changing from the inhalation phase to the exhalation phase, when the sensor 10 detects a given pressure value which corresponds to a change from the exhalation phase to the following inhalation phase, it sends this information to the drive means 12, which will then:

re-establish communication between the inhalation branch 2 and the balloons of the valves 9 and 3 by means of the solenoid valve 8, the result of which is to increase the pressure inside the balloons of the valves 9 and 3, and therefore close these valves, and stop the pressurized gas distributed by the first flow source 1 from being vented;

provide the first flow source 1 with a startup voltage value at least equal to the voltage of the turbine at the end of the preceding inhalation phase, which makes it possible to minimize the pressure rise time of the inhalation branch 2;

and reduce the value of the voltage of the second flow source 4, either to a zero value or to a preset value, as required.

When the voltage of the second flow source 4 is kept at a non-zero value during the inhalation phase, the gas which it delivers is fully vented to the atmosphere via the vent 11.

It is easy to see that, when changing from the exhalation phase to the following inhalation phase, given that the control voltage of the first flow source 1 is not zero, its inertia is commensurately reduced, which makes it possible for the pressure in the inhalation branch 2 to increase rapidly.

Figure 3:
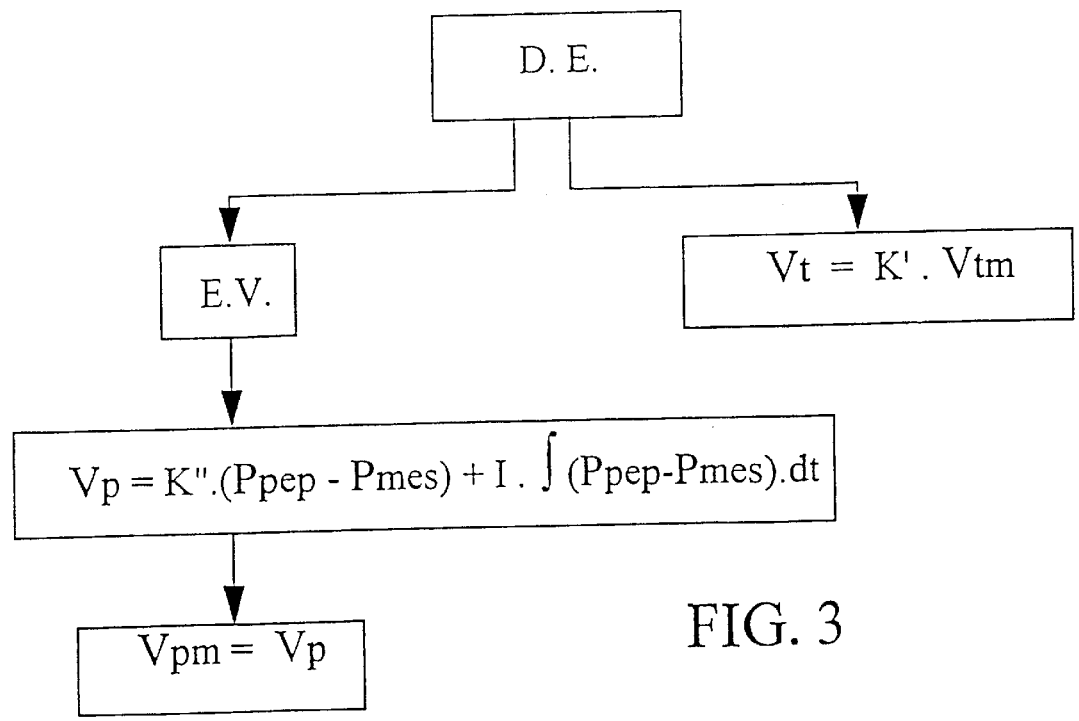

As schematized in FIG. 3, there are two consequences to the detection of exhalation (D. E.). On the one hand, the control voltage (Vt) of the first respiratory-flow source is kept at a value proportional (proportionality coefficient K') to the mean value of the control voltage (Vtm) of the first flow source, which was stored during the preceding inhalation phase, and, on the other hand, after the solenoid valve 8 has been switched, the control voltage (Vp) of the second respiratory-flow source is kept at a value proportional not only to the difference between the positive exhalation pressure (Ppep) and the measured pressure (Pmes), but also to the integral of the derivative of the difference between Ppep and Pmes during the exhalation time (respective proportionality coefficients: K" and I). The stored mean control voltage value (Vpm) of the second flow source is equal to Vp.

In FIGS. 2 and 3, the proportionality coefficients K, K" and I can be determined readily by the person skilled in the art. They will be chosen so as to obtain satisfactory, that is to say stable and rapid, regulation.

These various coefficients depend on parameters such as the length of the ducts, the characteristics of the equipment, etc.

Furthermore, when it is desired to obtain a rapid pressure rise for the first flow source during the inhalation phases, a coefficient K' equal to 1 will preferably be chosen.

Conversely, when a slower pressure rise is desired, a coefficient K' of less than 1 will be set.

What is claimed is:

1. Respiratory assistance device, comprising:
   an inhalation branch which is permanently connected, at its upstream end, to a first pressurized gas flow source and, at its downstream end, to a user's airways;
   at least a first exhalation valve and a second exhalation valve; said exhalation valves being arranged on said inhalation branch and controlled so that said exhalation valves are closed during a user's inhalation phase;
   a drive means for controlling the first pressurized gas flow source and delivering a stream of gas with substantially constant non-zero flow rate to the inhalation branch throughout a user's exhalation phase; and
   a detection means located in proximity to the downstream end of the inhalation branch, for detecting a user's respiratory activity, and sending a respiratory activity data item to the drive means.

2. The device according to claim 1, wherein the drive means control the first pressurized gas flow source in such a way as to deliver the stream of gas to the inhalation branch with a flow rate, during a user's exhalation phase, which is substantially equal to a flow rate delivered at the end of a user's preceding inhalation phase.

3. The device according to claim 1, wherein at least the first exhalation valve is arranged in proximity to the upstream end of the inhalation branch.

4. The device according to claim 1, wherein at least the second exhalation valve is arranged in proximity to the downstream end of the inhalation branch.

5. The device according to claim 1, further comprising a second pressurized gas flow source, and a distribution means; the second pressurized gas flow source and the distribution means being controlled by the drive means.

6. The device according to claim 5, wherein the detection means is a pressure sensor.

7. The device according to claim 5, wherein the exhalation valves are balloon pneumatic valves.

8. The device according to claim 7, wherein the distribution means is a solenoid valve.

9. The device according to claim 8, wherein during a user's inhalation phase, the solenoid valve establishes communication between the first pressurized gas flow source and the balloons of the pneumatic valves, so as to close said valves throughout a user's inhalation phase.

10. The device according to claim 8, wherein during a user's exhalation phase, the solenoid valve establishes communication between the second pressurized gas flow source and the balloons of the pneumatic valves, so as to control the opening of said valves.

11. The device according to claim 5, wherein the second pressurized gas flow source has a flow rate which is less than the flow rate from the first pressurized gas flow source.

12. The device according to claim 11, wherein a fraction of the gas delivered by the second pressurized gas flow source is discharged to the atmosphere via a vent.

13. The device according to claim 1, wherein the pressurized gas is air or oxygen-enriched air.

14. Method for using the device according to claim 1, wherein a control voltage of the first pressurized gas flow source is kept at a substantially constant and non-zero value throughout a user's exhalation phase.

15. The method according to claim 14, wherein throughout a user's exhalation phase, the control voltage of the first pressurized gas flow source is kept at a value substantially equal to the value which it had at the end of a user's preceding inhalation phase.

16. The method according to claim 15, wherein a user's exhalation is carried out under positive exhalation pressure.

* * * * *